United States Patent
Gordts et al.

(10) Patent No.: US 11,234,992 B2
(45) Date of Patent: Feb. 1, 2022

(54) METHODS AND THERAPIES FOR TREATING ATHEROSCLEROSIS AND/OR HYPERLIPIDEMIA USING OLIGOSACCHARIDES

(71) Applicant: The Regents of the University of California, Oakland, CA (US)

(72) Inventors: Philip Gordts, San Diego, CA (US); Ariane Pessentheiner, San Diego, CA (US); Lars Bode, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/289,288

(22) Filed: Feb. 28, 2019

(65) Prior Publication Data
US 2019/0269713 A1 Sep. 5, 2019

Related U.S. Application Data

(60) Provisional application No. 62/636,708, filed on Feb. 28, 2018.

(51) Int. Cl.
| | |
|---|---|
| *A61K 31/7016* | (2006.01) |
| *A61P 9/10* | (2006.01) |
| *A61P 3/06* | (2006.01) |
| *A61K 31/702* | (2006.01) |
| *A23L 33/125* | (2016.01) |
| *A61K 9/14* | (2006.01) |
| *A61K 9/48* | (2006.01) |
| *A61K 9/00* | (2006.01) |
| *A61K 9/20* | (2006.01) |

(Continued)

(52) U.S. Cl.
CPC ........ *A61K 31/7016* (2013.01); *A23L 33/125* (2016.08); *A61K 9/0095* (2013.01); *A61K 9/14* (2013.01); *A61K 9/20* (2013.01); *A61K 9/4808* (2013.01); *A61K 31/702* (2013.01); *A61K 35/20* (2013.01); *A61P 3/06* (2018.01); *A61P 9/10* (2018.01); *A23V 2002/00* (2013.01); *A23V 2200/326* (2013.01); *A23V 2200/3262* (2013.01); *A61K 45/06* (2013.01)

(58) Field of Classification Search
CPC ............. A61K 31/702; A61P 9/10; A61P 3/06
See application file for complete search history.

(56) References Cited

U.S. PATENT DOCUMENTS 9,669,050 B2 * 6/2017 Kang ................. A61K 31/7016
2009/0197806 A1 8/2009 Morrow et al.
(Continued)

FOREIGN PATENT DOCUMENTS

WO 2011/096809 A1 8/2011

OTHER PUBLICATIONS

Stella, V J, "Prodrugs as Therapeutics" Expert Opinion on Therapeutic Patents vol. 14 No. 3 pp. 277-280 (Year: 2004).*

(Continued)

*Primary Examiner* — Eric Olson
(74) *Attorney, Agent, or Firm* — Gavrilovich, Dodd & Lindsey LLP

(57) ABSTRACT

The disclosure provides for therapies and methods to treat atherosclerosis and/or hyperlipidemia, and complications resulting therefrom, with compositions that comprise therapeutically effective amounts of one or more human milk oligosaccharides.

5 Claims, 3 Drawing Sheets

(51) Int. Cl.
*A61K 35/20* (2006.01)
*A61K 45/06* (2006.01)

(56) References Cited

U.S. PATENT DOCUMENTS

| 2010/0075894 | A1  | 3/2010  | Hotamisligil et al. |
| 2011/0135717 | A1* | 6/2011  | Kang ............... A61K 31/7016 424/450 |
| 2014/0315781 | A1* | 10/2014 | Lee .................. A61K 47/61 514/1.1 |
| 2015/0064220 | A1  | 3/2015  | Thomas et al. |
| 2016/0113952 | A1* | 4/2016  | Dekany ............. C07H 3/06 514/54 |
| 2018/0305388 | A1* | 10/2018 | Abe .................. C07H 5/06 |

OTHER PUBLICATIONS

Silverman, "The Organic Chemistry of Drug Design and Drug Action" published 1992 by Academic press, ch. 8 pp. 352-397 (Year: 1992).*

Testa, "Prodrug Research: futile or fertile?" Biochemical Pharmacology vol. 68 pp. 2097-2106 (Year: 2004).*

Wolff, Burger's Medicinal Chemistry and Drug Discovery, fifth edition, vol. I, published by John Wiley & Sons, pp. 975-977 (Year: 1994).*

Vippagunta et al., "Crystalline Solids" Advanced Drug Delivery Reviews vol. 48 pp. 3-26 (Year: 2001).*

Braga et al., "Making Crystals from Crystals: a green route to crystal engineering and polymorphism" Chemical communications (2005) pp. 3635-3645 (Year: 2005).*

Ettmayer et al., "Lessons Learned from Marketed and Investigational Prodrugs" Journal of Medicinal Chemistry vol. 47 No. 10 pp. 2393-2404 (Year: 2004).*

Jain et al., "Polymorphism in Pharmacy" Indian Drugs vol. 23 No. 6 pp. 315-329 (Year: 1986).*

Lieberman et al., "Pharmaceuticl Dosage Forms" published by Marcel Dekker, INC, vol. 2 pp. 462-472 (Year: 1990).*

Haheim et al., "Primary Prevention of Cardiovascular Disease, with Emphasis on Pharmacological Interventions" Report from Norwegian Knowledge Centre for the Health Services (NOKC) No. 20-2008 (Year: 2008).*

Corti et al., "Lipid Lowering by Simvastatin Induces Regression of Human Atherosclerotic Lesions" Circulation vol. 106 issue 23 pp. 2884-2887 (Year: 2002).*

Copenheaver, Blaine R., International Search Report and Written Opinion, PCT/US2019/020133, United States Patent and Trademark Office, dated Jun. 25, 2019.

Wittmann-Regis, Agnes, International Preliminary Report on Patentability and Written Opinion, PCT/US2019/020133, The International Bureau of WIPO, dated Sep. 10, 2020.

* cited by examiner

METHODS AND THERAPIES FOR TREATING ATHEROSCLEROSIS AND/OR HYPERLIPIDEMIA USING OLIGOSACCHARIDES

CROSS REFERENCE TO RELATED APPLICATIONS

This application claims priority under 35 U.S.C. § 119 from Provisional Application Ser. No. 62/636,708, filed Feb. 28, 2018, the disclosures of which are incorporated herein by reference.

GOVERNMENT LICENSE RIGHTS

This invention was made with Government support under Grant No. HD089067 awarded by the National Institutes of Health. The Government has certain rights in the invention.

TECHNICAL FIELD

The disclosure provides for therapies and methods to treat atherosclerosis and/or hyperlipidemia and complications resulting therefrom by using one or more oligosaccharides.

BACKGROUND

Oligosaccharides are a group of complex sugars that are highly abundant in human milk. More than a hundred different oligosaccharides are found in human milk (HMOs). The amount and composition of HMOs are highly variable between women, and each structurally defined HMO might have a distinct functionality. HMOs are not digested by the infant and serve as metabolic substrates for select microbes, contributing to shaping the infant's gut microbiome. HMOs act as soluble decoy receptors that block the attachment of viral, bacterial or protozoan parasite pathogens to epithelial cell surface sugars, which may help prevent infectious diseases in the gut and also the respiratory and urinary tracts. HMOs are also antimicrobials that act as bacteriostatic or bactericidal agents. In addition, HMOs alter host epithelial and immune cell responses with potential benefits for the neonate.

SUMMARY

The disclosure provides methods and composition of oligosaccharides for treating or attenuating atherosclerosis, a disease that results in thickening of the arterial wall and narrowing of the arterial lumen leading to cardiovascular disease such as reduced blood flow to vital organs, unstable angina, myocardial infarction, sudden cardiac death or stroke. It was further found herein, that oligosaccharides found in human breast milk can be used to attenuate hyperlipidemia, including hypercholesterolemia, hypertriglyceridemia and a combination of both.

In in vitro and in vivo studies presented herein, 3'-sialyllactose (3'SL) and 6'-sialyllactose (6'SL) were found to attenuate inflammation in the liver, adipose tissue and arterial vessel wall and suppresses systemic secretion of pro-inflammatory cytokines like interleukin (IL)-1β and IL-6. Moreover, the results indicate, for example, that 3'-sialyllactose (3'SL) can improve lipid metabolism by promoting lipase activity as well postprandial lipid clearance.

The disclosure provides a method of treating or attenuating atherosclerosis and/or hyperlipidemia in a subject in need thereof comprising administering a composition comprising therapeutically effective amounts of one or more human milk-based oligosaccharides or analogs thereof. In one embodiment, the one or more human milk-based oligosaccharides are selected from 3'-fucosyllactose, 2'-fucosyllactose, 3'-sialyllactose, 6'-sialyllactose, lacto-N-tetraose, lacto-N-neotetraose, lacto-N-fucopentaose I, lacto-N-fucopentaose II, lacto-N-fucopentaose III, and/or lacto-N-fucopentaose V. In another or further embodiment, the one or more human milk-based oligosaccharides comprises 3'-sialyllactose and/or 6'-sialyllactose. In still a further embodiment, the one or more human milk-based oligosaccharides comprises 3'-sialyllactose. In yet another embodiment, the one or more human milk-based oligosaccharides comprises an oligosaccharide with a structure of Formula I(a):

Formula I

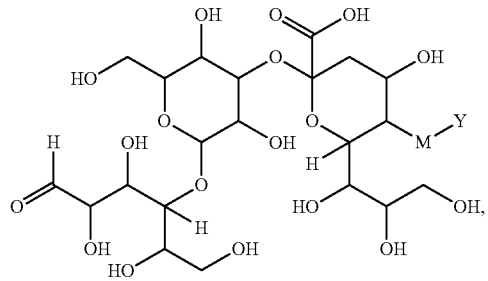

or a pharmaceutically acceptable salt, prodrug, or solvate thereof, wherein, M is selected from NH or O; and Y is selected from H, acetyl, alkyl, aryl, alkylaryl, arylalkyl, haloalkyl, and alkoxy. In a further embodiment, the one or more human milk-based oligosaccharides comprises an oligosaccharide with a structure of Formula I(a):

Formula I

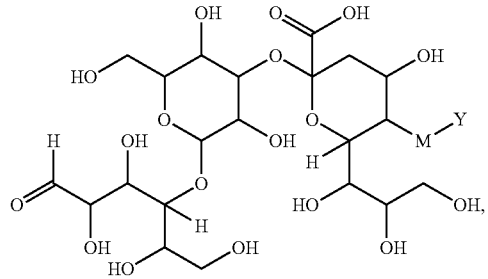

or a pharmaceutically acceptable salt, prodrug, or solvate thereof, wherein, M is NH; and Y is selected from

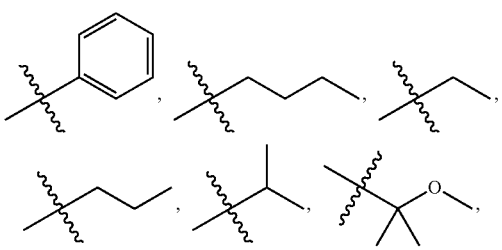

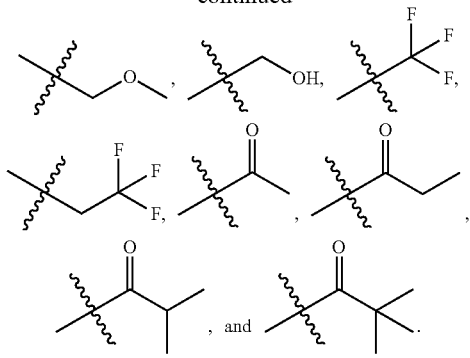

In a further embodiment, the one or more human milk-based oligosaccharides comprises an oligosaccharide with a structure of Formula I(a):

Formula I(a)

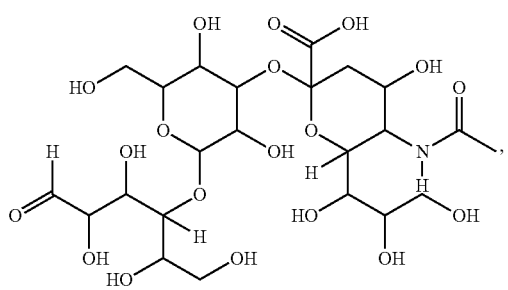

or a pharmaceutically acceptable salt, prodrug, or solvate thereof. In yet another or further embodiment, the one or more human milk-based oligosaccharides comprises an oligosaccharide with a structure of Formula I(b):

Formula I(b)

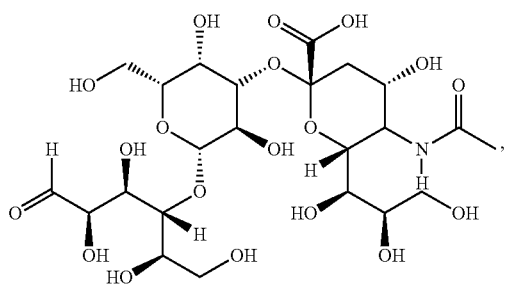

or a pharmaceutically acceptable salt, prodrug, or solvate thereof. In still another or further embodiment of any of the foregoing, the subject is an adult human subject.

The disclosure also provides a method of treating or attenuating one or more complications associated with atherosclerosis and/or hyperlipidemia in a subject in need thereof comprising administering a therapeutically effective amount of one or more human milk-based oligosaccharides. In another or further embodiment, the one or more complications associated with atherosclerosis and/or hyperlipidemia are selected from coronary artery disease, heart failure, myocardial infarction, aneurysm, stroke, arrhythmia, peripheral arterial disease, chronic kidney disease, end-stage renal disease, renal artery stenosis, central retinal artery occlusion, central retinal vein occlusion, branch retinal artery occlusion, branch retinal vein occlusion, erectile dysfunction, and mesenteric ischemia. In another or further embodiment of any of the foregoing, the administration of therapeutically effective amounts of one or more human milk-based oligosaccharides results in one of more of the following effects: a decrease in the incidence or severity of the atherosclerosis; a decrease in the size of aortic plaques; a decrease in the size of atherosclerotic lesions; a decrease in the plasma concentration for triglycerides; a decrease in the plasma concentration of cholesterol; a reduced incidence of complications resulting from atherosclerosis and/or hyperlipidemia; and/or an improvement in subject-reported outcomes as to the status of the subject's health condition. In another or further embodiment of any of the foregoing, the composition is a pharmaceutically acceptable composition comprising one or more pharmaceutically acceptable carriers and/or excipients. In a further embodiment, the pharmaceutically acceptable composition is formulated for oral delivery. In still a further embodiment, the pharmaceutically acceptable composition is formulated as a powder that is soluble in an aqueous solvent, a tablet, a chewable tablet or gummy, a liquid filed capsule or a capsule. In another embodiment, the pharmaceutically acceptable composition is formulated for parenteral administration. In yet another or further embodiment of any of the foregoing, the composition is administered in combination with one or more drugs or therapeutic agents selected from cholesterol medications, anti-platelet medications, beta blocker medications, angiotensin-converting enzyme (ACE) inhibitors, calcium channel blockers, and diuretics. In a further embodiment, the cholesterol medications are selected from HMG CoA reductase inhibitors, selective cholesterol absorption inhibitors, bile acid sequestrants, fibrates, niacin, and omega-3 fatty acid esters. In still a further embodiment, the HMG CoA reductase inhibitors are selected from atorvastatin, fluvastatin, lovastatin, pravastatin, rosuvastatin calcium, and simvastatin. In yet a further embodiment, the selective cholesterol absorption inhibitor is ezetimibe. In another embodiment, the bile acid sequestrants are selected from cholestyramine, colestipol, and colesevelam HCl. In yet another embodiment, the fibrates are selected from gemfibrozil, fenofibrate, and clofibrate. In still another embodiment, the anti-platelet medications are selected from acetylsalicylic acid, clopidogrel, prasugrel, and ticagrelor. In another embodiment, the beta blocker medications are selected from acebutolol, atenolol, betaxolol, bisoprolol fumarate, carteolol, esmolol, labetalol, metoprolol, nadolol, nebivolol, penbutolol, pindolol, propranolol, sotalol, and timolol. In yet another embodiment, the ACE inhibitors are selected from benazepril, captopril, enalapril, fosinopril, lisinopril, moexipril, perindopril, quinapril, ramipril, and trandolapril. In another embodiment, the calcium channel blockers are selected from amlodipine, diltiazem, isradipine, nicardipine, nifedipine, nisoldipine, and verapamil. In yet another embodiment, the diuretics are selected from chlorothiazide, chlorthalidone, indapamide, hydrochlorothiazide, methylclothiazide, metolazone, bumetanide, furosemide, ethacrynate, torsemide, amiloride hydrochloride, spironolactone, and triamterene.

The disclosure also provides food and/or beverage compositions comprising an oligosaccharide of the disclosure as a fortifying agent of the food or beverage. In one embodiment, the disclosure provides a food additive consisting of 3'SL and/or 6'SL. In another embodiment, the disclosure provides a carbonated beverage containing 3'SL and/or 6'SL.

In yet another embodiment the disclosure provides a non-human milk composition fortified with 3'SL and/or 6'SL. In yet another embodiment, the disclosure provides a non-milk composition fortified with one or more human milk oligosaccharides. In a specific embodiment, the non-milk composition is fortified with 3'SL and/or 6'SL.

DETAILED DESCRIPTION

Figure 1:
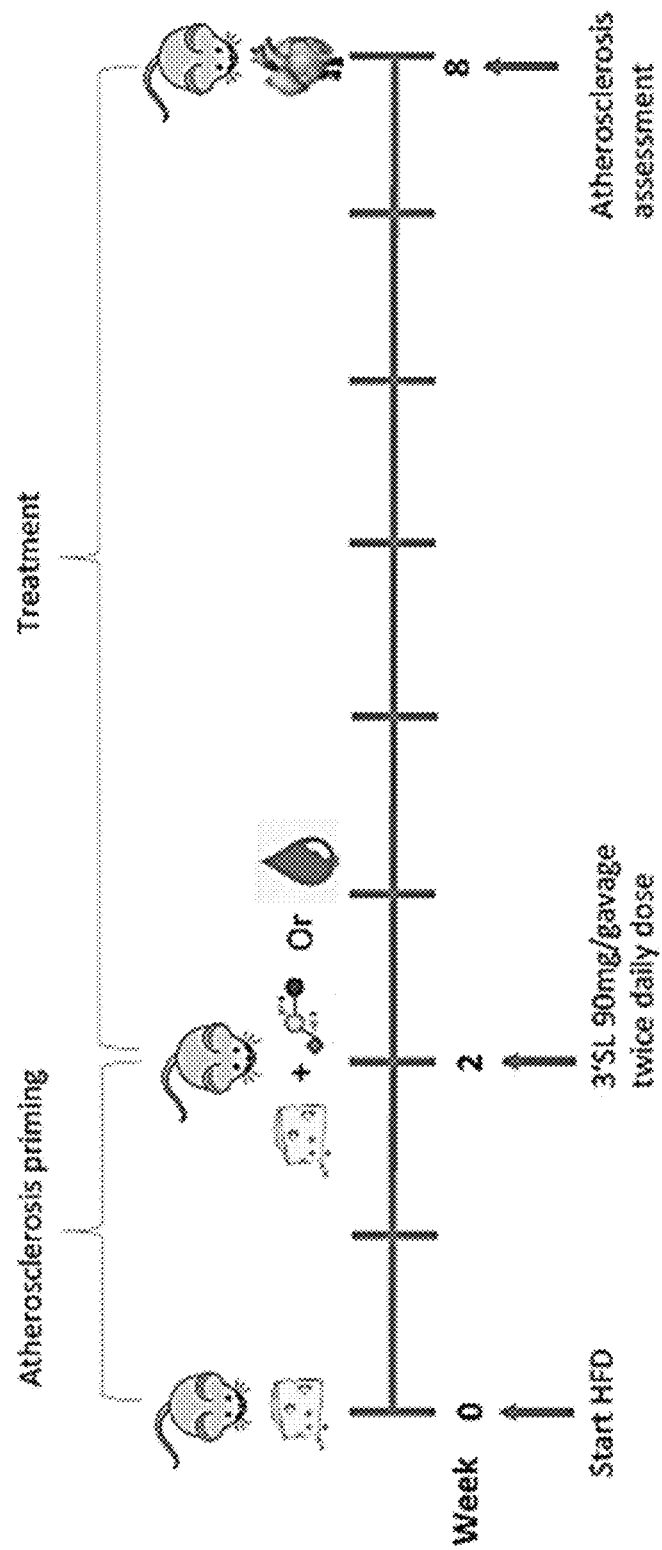
FIG. 1 provides a diagram of a mouse model used to test 3'SL effects on atherosclerosis. In particular, the mice are fed a high fat diet for two weeks prior to treatment in order to promote atherosclerosis in the mice. Treatment begins at the end of the second week with 3'SL or vehicle, whereby 3'SL or vehicle are administered to the mice twice daily at a dose of 90 mg/gavage. After 6 weeks of treatment, the mice are sacrificed and atherosclerosis lesions and plaques are assessed.

As used herein and in the appended claims, the singular forms "a," "an," and "the" include plural referents unless the context clearly dictates otherwise. Thus, for example, reference to an "atherosclerotic plaque" includes a plurality of atherosclerotic plaques and reference to "a human milk oligosaccharide" includes reference to one or more human milk oligosaccharides and equivalents thereof known to those skilled in the art, and so forth.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

All publications mentioned herein are incorporated herein by reference in full for the purpose of describing and disclosing the methodologies, which are described in the publications, which might be used in connection with the description herein. Moreover, with respect to any term that is presented in one or more publications that is similar to, or identical with, a term that has been expressly defined in this disclosure, the definition of the term as expressly provided in this disclosure will control in all respects.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

A "disorder" or "disease" is any condition that would benefit from treatment with the compositions and/or methods of the disclosure. An example of disorders and diseases that can be treated with the compositions and/or methods disclosed herein, include atherosclerosis and/or hyperlipidemia and complications resulting therefrom, including, but not limited to, coronary artery disease, heart failure, myocardial infarction, aneurysm, stroke, arrhythmia, peripheral arterial disease, chronic kidney disease, end-stage renal disease, renal artery stenosis, central retinal artery occlusion, central retinal vein occlusion, branch retinal artery occlusion, branch retinal vein occlusion, erectile dysfunction, and mesenteric ischemia.

An "effective amount" refers to an amount effective, at dosages and for periods of time necessary, to achieve the desired therapeutic or prophylactic result.

The term "human milk oligosaccharides (HMO)" refers generally to a number of complex carbohydrates found in human milk. Among the monomers of milk oligosaccharides are D-glucose (Glc), D-galactose (Gal), N-acetylglucosamine (GlcNAC), L-fucose (Fuc), and sialic acid [N-acetylneuraminic acid (NeuAc)]. Elongation may be achieved by attachment of GlcNAc residues linked in $\beta$1-3 or $\beta$1-4 linkage to a Gal residue followed by further addition of Gal in a $\beta$-1-3 or $\beta$-1-4 bond. Most HMOs carry lactose at their reducing end. From these monomers, a large number of core structures may be formed. Further variations may occur due to the attachment of lactosamine, Fuc, and/or NeuAc. See, e.g., Kunz, C. et al., *Annual. Rev. Nutri.* 20:699-722 (2000), for a further description of HMOs. In a specific embodiment, a HMO is 3'SL and/or 6'SL.

The term "isolated," when applied to an oligosaccharide, denotes that the oligosaccharide is essentially free of other milk components with which it is associated in the natural state, i.e., in human breast milk. It can be in, for example, a dry or aqueous solution.

The term "purified" denotes that an oligosaccharide has been separated at least in part from other components of human breast milk. Particular oligosaccharides can be purified individually or a combination of oligosaccharides can be purified away from at least one other component of milk. In some embodiments, the oligosaccharide can be at least 85% pure, optionally at least 95% pure, and optionally at least 99% pure.

An "individual," "subject," or "patient" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, a mammal is a human.

The term "substantially similar" or "substantially the same," as used herein, denotes a sufficiently high degree of similarity between two numeric values, between two sequences, between to ranges, between to compositions and the like (for example, one associated with an oligosaccharide of the disclosure and the other associated with a reference oligosaccharide), such that one of skill in the art would consider the difference between the two to be of little or no biological and/or statistical significance within the context of the biological characteristic measured by the values. The difference between two values is, for example, less than about 50%, less than about 40%, less than about 30%, less than about 20%, and/or less than about 10% as a function of the reference value.

The phrase "substantially reduced," or "substantially different," as used herein, denotes a sufficiently high degree of difference between two numeric values (generally one associated with an oligosaccharide and the other associated with a reference oligosaccharide) such that one of skill in the art would consider the difference between the two values to be of statistical significance within the context of the biological characteristic measured by said values. The difference between said two values is, for example, greater than about 10%, greater than about 20%, greater than about 30%, greater than about 40%, and/or greater than about 50% as a function of the value for the reference oligosaccharide.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In certain embodiments, one or more oligosaccharides of the disclosure are used to prevent, treat, or attenuate atherosclerosis and/or hyperlipidemia, or complications resulting therefrom, in a patient in need thereof.

An oligosaccharide that "naturally occurs in human breast milk" refers to an oligosaccharide that can be detected in human breast milk, for example, detected by FTICR MS as described herein. Although an oligosaccharide naturally occurs in human breast milk, i.e., an oligosaccharide of the same structure can be detected in human breast milk, an oligosaccharide can be produced synthetically and nevertheless be detected in human breast milk.

An oligosaccharide that does "not naturally occur in human breast milk" refers to an oligosaccharide that cannot be detected in human breast milk. For example, the oligosaccharide may be isolated and/or purified from non-humans, or may be artificially synthesized.

In the United States and most other developed countries, atherosclerosis is the leading cause of illness and death. In 2015, cardiovascular disease, primarily coronary artery disease (atherosclerosis that affects the arteries supplying blood to the heart) and stroke, caused almost 15 million deaths worldwide, making atherosclerosis the leading cause of death worldwide.

Atherosclerosis means hardening of the arteries due to the presence of plaques, which are deposits of fatty materials. Atherosclerosis can affect the medium-sized and large arteries of the brain, heart, kidneys, other vital organs, and legs.

Atherosclerosis begins when an injured artery wall creates chemical signals that cause certain types of white blood cells (monocytes and T cells) to attach to the wall of the artery. These cells move into the wall of the artery. There they are transformed into foam cells, which collect cholesterol and other fatty materials and trigger growth of smooth muscle cells in the artery wall. In time, these fat-laden foam cells accumulate. They form patchy deposits (atheromas, also called plaques) covered with a fibrous cap in the lining of the artery wall. With time, calcium accumulates in the plaques. Plaques may be scattered throughout medium-sized and large arteries, but they usually start where the arteries branch. Existing treatment options for atherosclerosis and cardiovascular disease are aimed at lowering Low-density lipoprotein (LDL) cholesterol by either increasing hepatic LDLR expression by using statins and PCSK9 inhibitors, or by reducing cholesterol absorption by using ezetimibe. Further development of therapeutic strategies is warranted due to various drawbacks and limitations using the current therapeutic options, including (i) persisting residual risk in patients with substantial LDL cholesterol reduction; (ii) incremental increase of cardiovascular disease risk with each additional feature of the Metabolic Syndrome; (iii) the difficulty to achieve present LDL-cholesterol goals; (iv) intolerance and aversion to cholesterol lowering drugs; (v) high cost of these therapies; and (iv) the expanding target population.

As the etiologies between hyperlipidemia and atherosclerosis largely overlap, one can treat hyperlipidemia using the same therapies listed above for atherosclerosis. For example, current therapeutic interventions for hypercholesterolemia are aimed at lowering Low-density lipoprotein (LDL) cholesterol that either increase hepatic LDLR expression (statins and PCSK9 inhibitors) or reducing cholesterol absorption (ezetimibe). Current therapeutic interventions for hypercholesterolemia differ in that fibric acid derivatives, niacin, and omega-3 fatty acids are preferred over using high doses statins to lower triglyceride levels. Like with atherosclerosis, further development of novel therapeutic strategies is warranted because of (i) the difficulty to achieve present LDL-cholesterol and triglyceride goals; (ii) intolerance and aversion to cholesterol lowering drugs; (iii) high cost of these therapies; and (iv) the expanding target population.

Given that inflammation plays a key role in all stages of atherosclerosis, preventing further infiltration and production of macrophages and their subsequent cytokine secretion are considered valid therapeutic strategies. Macrophages play a central role in both acute and chronic inflammation and have remarkable plasticity when it comes to their inflammatory phenotype. Naïve macrophages are directed to distinct phenotypic programs designated as classically activated pro-inflammatory macrophages (M1) or alternatively activated resolving macrophages (M2). The transition of a naïve macrophage to an M1 phenotype is mediated by lipopolysaccharides (LPS) as well as cytokines produced by Th1 lymphocytes, such as interferon (IFN)-γ and tumor necrosis factor (TNF)-α. Acute inflammation is a protective response to extreme challenges to homeostasis, such as infection, tissue stress, and injury and requires in a first phase infiltration of M1 macrophages to clear the danger followed by a second resolution phase of 'Healing type' M2 macrophages infiltrating the inflammation site leading to repair and maintain tissue integrity. However, the system has the potential to become locked in a state of chronic inflammation that can be described as a non-resolving inflammation resulting in persistence of M1 macrophage infiltration. The continuous flow of M1 macrophage secreting cytokines such as interleukin (IL)-1β and IL-6 are of major etiological importance in atherosclerosis, autoimmunity, and other chronic inflammatory conditions. Preventing further infiltration and production of M1 macrophages and more importantly the secretion of their cytokines is considered valid therapeutic strategies to treat hyperlipidemia and/or atherosclerosis, and complications resulting therefrom.

Clinical trials are currently testing the proposition that targeting inflammation can reduce cardiovascular disease events in humans by (i) blocking IL1 receptor (e.g., using Anakinra), (ii) neutralizing IL-1β (e.g., using Canakinumab) or (iii) administering low-doses of methotrexate. Both methotrexate and Anakinra target IL-1β, but also affect IL6 and TNFα expression. Targeted inhibition of IL-6 and TNFα can be achieved by using monoclonal antibodies (Tocilizumab and Adalimumab, respectively). Such antibody therapies require regular injections, and are currently only approved to treat arthritis. The antibodies do not meaningfully impact LDL cholesterol and apolipoprotein levels, however. Adverse effects, high costs and administration via injections limit the usefulness of the antibody therapies. Further, the antibody therapies have not been approved by the FDA for treating cardiovascular disease.

So far, human milk oligosaccharides (HMOs) have only been implicated in preventing diseases and improving health of newborns and infants, and to prevent infection by the HIV-1 virus. A therapeutic effect on cardiovascular disease has not yet been described for human milk oligosaccharides. Thus, the use of HMOs, including analogs a derivatives thereof, for treating atherosclerosis and/or hyperlipidemia and complications resulting therefrom, have notable advantages, including, but not limited to: (a) HMOs are naturally found in human milk, thus, HMOs are safe for human consumption; (b) HMOs can be administered orally; (c) can be used safely with pregnant women with cardiovascular disease. Pregnant women with cardiovascular disease pose a particular therapeutic challenge, some cardiovascular disease drugs can cross the placenta and harm the fetus and/or are transferred into breast milk and harm the breastfed baby. HMOs, however, are already naturally present in breast milk. In fact, it can be found in the maternal systemic circulation already during pregnancy. Mothers, the growing fetus and the newborn infant are already exposed to HMOs and unlike many other existing drugs, HMOs would not cause any harm to these vulnerable populations. Moreover, the use of HMOs for treating atherosclerosis and/or hyperlipidemia and complications resulting therefrom, have the further advantages of: (d) HMO therapy could be used as an adjunct to existing therapies and should be well tolerated by patients of either sex and will not necessarily be limited to pregnant or lactating patient; (e) the natural occurrence in human milk qualifies HMOs to receive FDA GRAS (Generally Regarded As Safe) status in the US and Novel Food status in the European Union for oral application in both infants and adults; and (f) new technologies for large-scale production in bioengineered microbes make individual HMOs like 3'SL not only available, but also commercially viable. Other HMOs like 2'-fucosyllactose and lacto-N-neotetraose are already synthesized at large scale and at low cost. For example, 2'-fucosyllactose is now added to commercially available infant formula (Similac, Abbott Nutrition), a market that does not allow for high ingredient costs. Unlike many of the other currently existing drugs for treating atherosclerosis and hyperlipidemia, HMOs, like 3'SL, are a low cost therapeutic option.

Moreover, as demonstrated in the studies presented herein, HMOs have been found to attenuate inflammatory effects promoted or mediated by macrophages. As such, HMOs (e.g., 3'SL) can be used to treat other inflammatory mediated diseases and disorders in addition to atherosclerosis, such as rheumatoid arthritis, chronic obstructive pulmonary disease, insulin resistance, type-2 diabetes, obesity, systemic juvenile idiopathic arthritis, etc.

As demonstrated in the studies presented herein, oligosaccharides of the disclosure have been found to attenuate hyperlipidemia and atherosclerosis in mice models. The oligosaccharides of the disclosure are oligosaccharides that naturally occur in human breast milk, or derived therefrom. Oligosaccharides that naturally occur in human breast milk, also referred to as human milk oligosaccharides (HMOs), are a group of ~150 different complex sugars found in human milk. HMOs form the third most abundant solid component of human milk after lactose and fat with typical concentrations between 10 to 15 g/L in mature term milk. HMOs function as a prebiotic helping to establish commensal bacteria. HMOs also function as anti-adhesives that help prevent the attachment of microbial pathogens to mucosal surfaces. HMOs have been implicated in modulating responses of the epithelium and of the immune cells, reducing excessive mucosal leukocyte infiltration and activation, and lowering the risk for necrotizing enterocolitis and possibly also providing infants with sialic acid as a potentially essential nutrient for brain development and cognition. Specific examples of HMOs include 3'-fucosyllactose, 2'-fucosyllactose, 3'-sialyllactose, 6'-sialyllactose, lacto-N-tetraose, lacto-N-neotetraose, lacto-N-fucopentaose I, lacto-N-fucopentaose II, lacto-N-fucopentaose III, and lacto-N-fucopentaose V. In a particular embodiment, an oligosaccharide of the disclosure is 3'-sialyllactose (3'SL). 3'-Sialyllactose ($\alpha$-NeuNAc-(2→6)-$\beta$-D-Gal-(1→4)-D-Glc) is a compound wherein the acetylneuraminyl (NANA) unit is connected to the galactosyl unit of lactose at the 3' position. In 6'-sialyllactose, this connection is at the 6' position.

Further, derivatives of oligosaccharides of disclosure may be made by covalent linking an oligosaccharide to any other chemical compound or polymer, using methods known in the art of organic and synthetic chemistry or through enzymatic methods. These derivatives include, but are not limited to, attaching or covalently linking the oligosaccharides of the disclosure to other oligosaccharides, amino acids, polypeptides, and nucleic acids.

Further, isomer, analog and derivatives of the oligosaccharides of the disclosure may be made by substituting a sugar residue within an oligosaccharide disclosed herein with a sugar analog. For example, galactose may be substituted with its analogs, including but not limited to 2-desoxy-D-galactose, 2-desoxy-2-fluoro-D-galactose and 2-desoxy-2-amino-D-galactose. For example, glucose may be substituted with its analogs, including, but not limited to, 2-Deoxy-D-glucose, 2,2-difluoro-deoxy-D-glucose, 2-deoxy-2-fluoro-2-iodo-D-glucose, 1-O-methyl-D-glucose, 2-O-methyl-D-glucose, 2-deoxy-2-chloro-D-glucose, 2-deoxy-2-bromo-D-glucose, 3-O-$^{11}$C-methyl-D-glucose, 6-deoxy-D-glucose, 6-deoxy-6-fluoro-D-glucose, and 6-deoxy-6-iodo-D-glucose, and 2-deoxy-2-$^{18}$F-fluoro-D-glucose. For example, N-acetylglucosamine may be substituted with its analogs, N-acetylglucosaminylasparagine, N-acetylglucosamine 6-sulfate, N-acetylglucosamine-1-phosphate, N-acetylglucosamine 6-phosphate, methyl-2-acetamido-2-deoxy-D-glucopyranoside, N-acetylglucosaminitol, N-bromoacetylglucosamine, 2-acetamido-1,3,6-tri-O-acetyl-4-deoxy-4-fluoroglucopyranose, N-acetylglucosamine thiazoline, N-fluoroacetyl-D-glucosamine, 2-acetamido-2-deoxy-D-glucono-(1,5)-lactone, and 3-acetamido-3,6-dideoxyglucose.

Furthermore, isomers of an oligosaccharide of the disclosure may be obtained based on a chiral center, such that D-glucose as a six-member ring can exist either as $\alpha$-D-glucopyranose or $\beta$-D-glucopyranose, depending on the orientation of the hydroxyl group at the C-1 position with respect to the rest of the ring. Similarly, D-galactose, N-acetylglucosamine and sialic acid rings may exist in either $\alpha$- or $\beta$-conformation. The isomers of an oligosaccharide may differ based on $\alpha$- or $\beta$-position of the acetal functional groups. For example, the glycosidic linkage between galactose and glucose may be $\alpha$-acetal functional group instead of $\beta$-acetal functional group, e.g., an $\alpha$1,4 glycosidic linkage instead of a β1,4 glycosidic linkage. Thus, a number of isomers of the oligosaccharide may exist based on the orientation of the hydroxyl-group at the C-1 or C-2 position of the six-member rings.

Since modification by sialic acid introduces a negative charge in the form of a carboxyl-group (COO—), other monosaccharides also contain carboxyl-groups and may substitute for sialic acid in an oligosaccharide of the disclosure variant, isomer, analog and derivatives thereof. These sugars could be glucuronic acid, galacturonic acid, iduronic acids, 3-Deoxy-D-manno-oct-2-ulosonic acid, neuraminic acid, or any other carboxyl-group containing monosaccharides or derivatives thereof.

Variants, analogs and derivatives including its isomers and metabolites can be produced by modifying an oligosaccharide disclosed herein through substitutions, modifications, and conjugations that preserve the biological activity of preventing or inhibiting atherosclerosis and/or hyperlipidemia in a subject, including adult human subjects.

As used herein, suitable or effective amounts of oligosaccharide disclosed herein means an amount sufficient to inhibit or attenuate atherosclerosis and/or hyperlipidemia. Examples of suitable amounts include, but are not limited to, 250 mg, 400 mg, 500 mg, 600 mg, 700 mg, 750 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, 2500 mg, and a range including or between any two of foregoing values. In some embodiments, these amounts or ranges may vary by about 5%, about 10%, about 15%, about 20%, or a range including or between any two of the foregoing percentages.

Figure 2A:
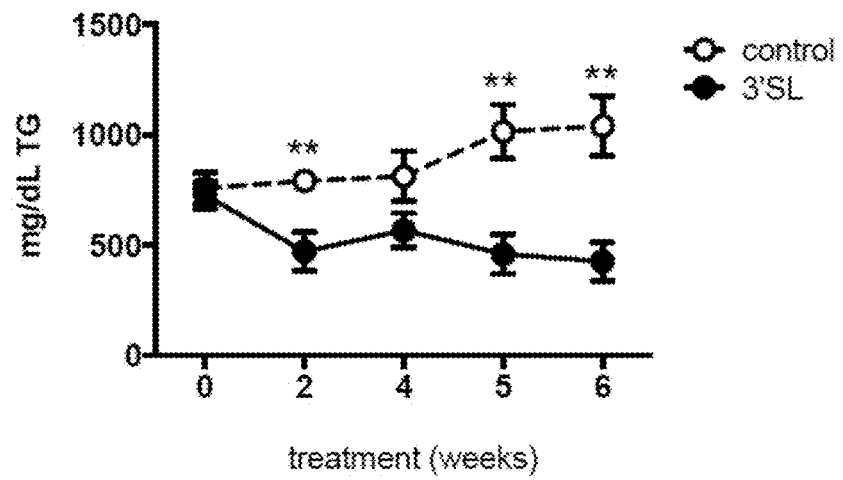
FIG. 2A-B demonstrates the effect of 3'SL on attenuating hyperlipidemia, including hypercholesterolemia, and hypertriglyceridemia. (A) Mice were assessed for the levels of triglycerides when fed a high fat diet and treated with 3'SL or vehicle. As shown, mice that were administered 3'SL had lower plasma triglyceride levels than the control mice. (B) The cholesterol levels of mice were also assessed. As shown, mice that were administered 3'SL had lower cholesterol levels than the control mice.
Figure 2B:
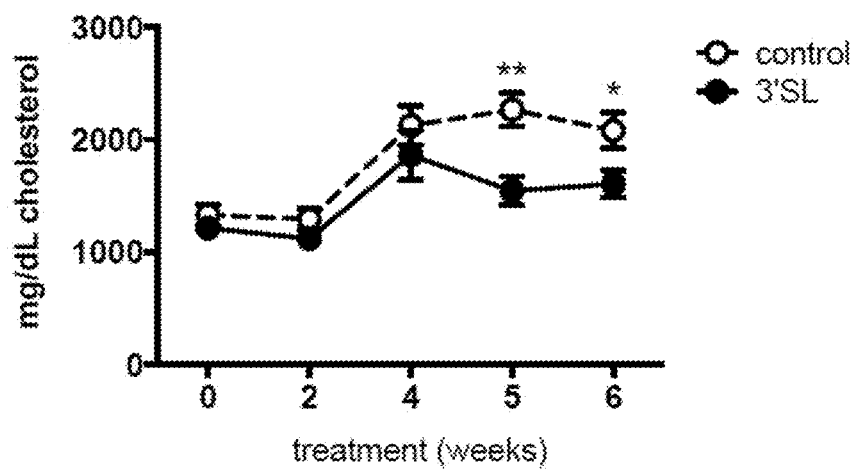
Figure 3A:
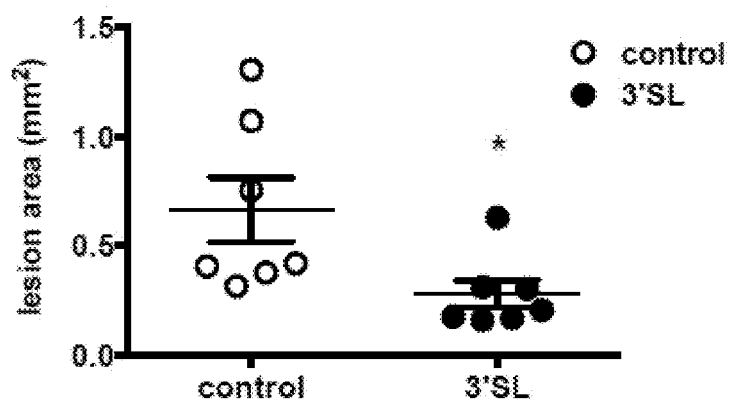
FIG. 3A-B demonstrates the effect of 3'SL on attenuating atherosclerosis in mice. (A) Mice were En Face analyzed for atherosclerotic lesions when fed a high fat diet and treated with 3'SL or vehicle. As indicated, mice that were administered 3'SL had smaller lesion areas than the control mice. (B) The sizes of the aortic plaque were also assessed in the mice. As indicated, mice that were administered 3'SL had smaller sized plaques than the control mice.
Figure 3B:
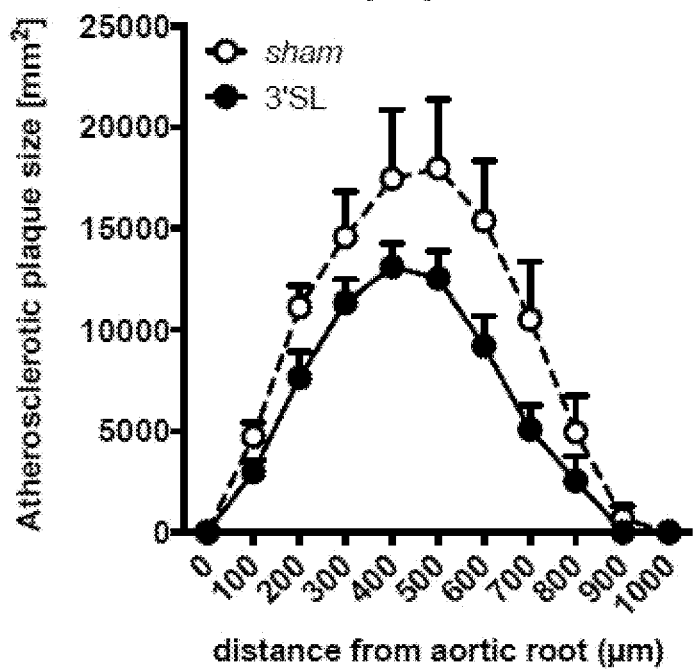

Further, in vitro and in vivo studies presented herein, have indicated that the administration of therapeutically effective doses of an oligosaccharide of the disclosure attenuated atherosclerosis and hyperlipemia. In particular, pooled HMOs (~100 μg/mL) attenuated LPS-induced M1 polarization and importantly its subsequent cytokine expression (IL-1β, IL-6, etc. mRNA and protein levels) in a mouse macrophage cell line (RAW246) and in primary bone marrow derived macrophages (BMDM). It was further found that 3'sialyllactose (3'SL) had and $IC_{50}$[IL-6]~16.5 μg/mL and an $IC_{50}$ [IL-1β]~44.4 μg/mL. 6'sialyllactose (6'SL) was also shown to have the a therapeutic effect. Moreover, the attenuation effects remain when cells are stimulated with LipidA instead of LPS, excluding carbohydrate-carbohydrate interactions between LPS and HMOs above the cell surface. 3'SL both in the absence and presence of LPS engaged with plasma membrane proteins on BMDM to regulate down-stream activation of the MAPK pathway but not the NFκ-β pathway. 3'SL also effectively reduced cytokine expression in LPS-activated Thp-1 cells (human cell line), showing that the effects are not mouse-specific and translate to human cells. In vivo models further showed that administration of 3'SL to mice on a high fat diet (HFD) resulted in a significant decrease in the levels for triglycerides (TG) in comparison to mice that were not similarly treated with 3'SL (see FIG. 2A). Moreover, administration of 3'SL to mice on a high fat diet (HFD) also resulted in a significant decrease in the levels for cholesterol in comparison to mice that were not similarly treated with 3'SL (see FIG. 2B). The lesion area for atherosclerotic lesions were significantly reduced in size in mice treated with 3'SL in comparison to untreated control mice (see FIG. 3A). Similarly, aortic plaque size was significantly reduced in mice treated with 3'SL in comparison to sham treated control mice (see FIG. 3B).

In a particular embodiment, the disclosure provides for treating or attenuating atherosclerosis and/or hyperlipidemia in a subject in need thereof, with an effective amount of one or more oligosaccharides disclosed herein. In a further embodiment, the one or more oligosaccharides are human milk oligosaccharides (HMOs) or derivatives made therefrom. Specific examples of HMOs include 3'-fucosyllactose, 2'-fucosyllactose, 3'-sialyllactose, 6'-sialyllactose, lacto-N-tetraose, lacto-N-neotetraose, lacto-N-fucopentaose I, lacto-N-fucopentaose II, lacto-N-fucopentaose III, and lacto-N-fucopentaose V. In a particular embodiment, an oligosaccharide of the disclosure is 3'-sialyllactose (3'SL) or 6'-sialyllactose (6'SL). In a further embodiment, one or more oligosaccharides disclosed herein comprises 3'-sialyllactose (3'SL) and/or 6'-sialyllactose (6'LS) or a derivative thereof. In a further embodiment, the disclosure provides for an oligosaccharide having a structure of Formula I:

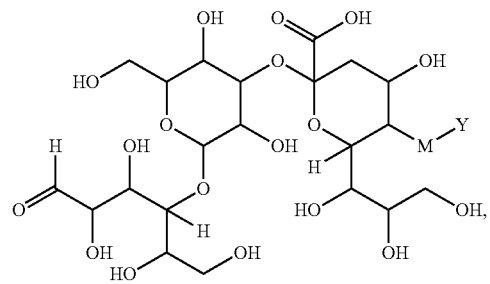

Formula I or a pharmaceutically acceptable salt, prodrug, or solvate thereof, wherein,
M is selected from NH or O; and
Y is selected from H, acetyl, alkyl, aryl, alkylaryl, arylalkyl, haloalkyl, and alkoxy. In yet a further embodiment, Y is selected from

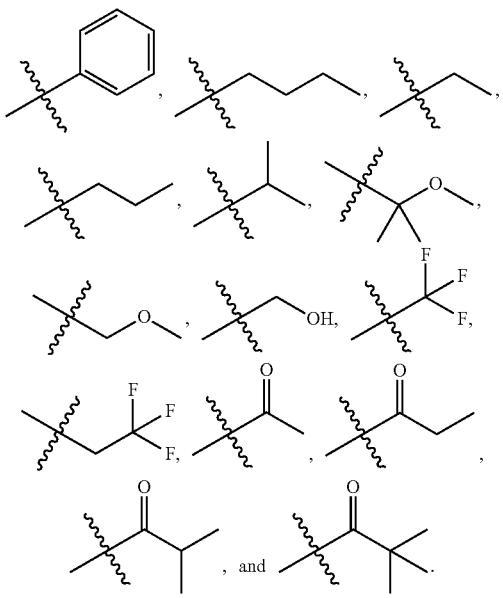

In another embodiment, the disclosure provides for an oligosaccharide having a structure of Formula I(a):

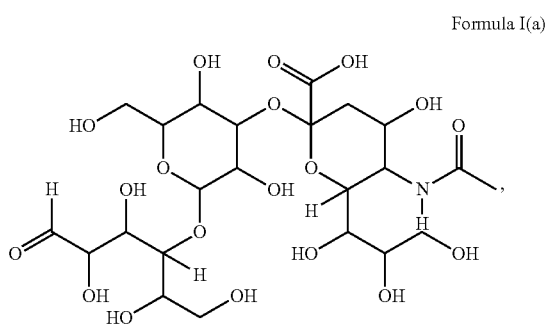 [SMILES: CC(=O)NC1C(O)CC(OC2C(O)C(CO)OC(OC(C(O)CO)C(O)C(O)C=O)C2O)(C(=O)O)OC1C(O)C(O)CO]

Formula I(a)

or a pharmaceutically acceptable salt, prodrug, or solvate thereof.

In yet another embodiment, the disclosure provides for an oligosaccharide having a structure of Formula I(b):

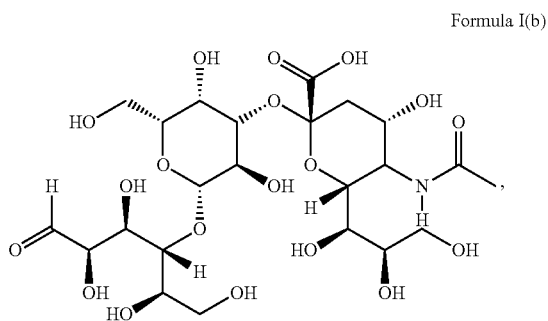

Formula I(b)

or a pharmaceutically acceptable salt, prodrug, or solvate thereof.

The oligosaccharides of the disclosure can be derived using any of a number of sources and methods known to those of skill in the art. For example, oligosaccharides disclosed herein can be purified from human milk using methods known in the art. One such method for extraction of oligosaccharides from pooled mother's milk entails the centrifugation of milk at 5,000×g for 30 minutes at 4° C. and fat removal. Ethanol is then added to precipitate proteins. After centrifugation to sediment precipitated protein, the resulting solvent is collected and dried by rotary evaporation. The resulting material is adjusted to the appropriate pH of 6.8 with phosphate buffer and β-galactosidase is added. After incubation, the solution is extracted with chloroform-methanol, and the aqueous layer is collected. Monosaccharides and disaccharides are removed by selective adsorption of the oligosaccharides using solid phase extraction with graphitized nonporous carbon cartridges. The retained oligosaccharides can be eluted with water-acetonitrile (60:40) with 0.01% trifluoroacetic acid (see, e.g., Ward et al., *Appl. Environ. Microbiol.* 72: 4497-4499 (2006)); Gnoth et al., *J. Biol. Chem.*, 276:34363-34370 (2001)); Redmond and Packer, *Carbohydr. Res.*, 319:74-79 (1999)). Individual oligosaccharides can be further separated using methods known in the art such as capillary electrophoresis, HPLC (e.g., high-performance anion-exchange chromatography with pulsed amperometric detection; HPAEC-PAD), and thin layer chromatography. See, e.g., Splechtna et al., *J. Agricultural and Food Chemistry* 54: 4999-5006 (2006). This process can provides substantially pure oligosaccharides being at least 50% pure of other material present in the raw mile, or at least 60%, 70%, 80%, 85%, 90%, 95%, 98%, 99% or 100% pure. In yet another embodiment, the process can provide purification of individual oligosaccharide "types" (e.g., 3'SL or 6'SL). The method can provide a specific oligosaccharide being at least 50% pure of other material present in the raw mile, or at least 60%, 70%, 80%, 85%, 90%, 95%, 98%, 99% or 100% pure of any other oligosaccharide or other component of raw milk.

Alternatively, enzymatic methods can be used to synthesize the oligosaccharides of the disclosure. In general, any oligosaccharide biosynthetic enzyme or catabolic enzyme (with the reaction running in reverse) that converts a substrate into any of oligosaccharide structures disclosed herein (or their intermediates) may be used. For example, prebiotic galacto-oligosaccharides have been synthesized from lactose using the β-galactosidase from *L. reuteri* (see, Splechtna et al., *J. Agricultural and Food Chemistry* 54: 4999-5006 (2006)). The reaction employed is known as transgalactosylation, whereby the enzyme β-galactosidase hydrolyzes lactose, and, instead of transferring the galactose unit to the hydroxyl group of water, the enzyme transfers galactose to another carbohydrate to result in oligosaccharides with a higher degree of polymerization (Vandamme and Soetaert, *FEMS Microbiol. Rev.* 16:163-186 (1995)). The transgalactosylation reaction can proceed intermolecularly or intramolecularly. Intramolecular or direct galactosyl transfer to D-glucose yields regioisomers of lactose. Through intermolecular transgalactosylation di-, tri-, and tetra saccharides and eventually higher oligosaccharides specific to Bifidobacteria are produced. A related method utilizes the β-galactosidase of *Bifidobacterium bifidum* NCIMB 41171 to synthesize prebiotic galacto-oligosaccharides (see, Tzortzis et al., *Appl. Micro. and Biotech.* 68:412-416 (2005)).

Another approach to the synthesis of the oligosaccharides of the disclosure that combines elements of the methods outlined above entails the chemical or enzymatic synthesis of or isolation of oligosaccharide backbones containing Lacto-N-biose, or Lacto-N-tretrose from non-human mammalian milk sources (e.g., cows, sheep, buffalo, goat, etc.) and enzymatically adding Lacto-N-biose, Fucose and Sialic Acid units as needed in order to arrive at an oligosaccharide of the disclosure. For this purpose, a variety of bifidobacterial carbohydrate modifying enzymes, such as those disclosed in PCT Publication WO 2008/033520 can be utilized. Examples of such oligosaccharide modifying enzymes include sialidases, silate O-Acetylesterases, N-Acetylneuraminate lyases, N-acetyl-beta-hexosaminidase, beta-galactosidases, N-acetylmannosamine-6-phosphate 2-epimerases, alpha-L-fucosidases, and fucose dissimilation pathway proteins, among others, which may be used to catalyze a biosynthetic reaction under the appropriate conditions.

Alternatively, conventional chemical methods may be used for the de novo organic synthesis of or conversion of pre-existing oligosaccharides into the oligosaccharides of the disclosure. See, e.g., March's Advanced Organic Chemistry: Reactions, Mechanisms, and Structure, 5th Edition.

New technologies for large-scale production in bioengineered microbes make individual HMOs like 3'SL not only available, but also commercially viable. Other HMOs like 2'-fucosyllactose and lacto-N-neotetraose are already synthesized at large scale and at low cost.

While it may be possible for the oligosaccharides of the disclosure to be administered as raw chemicals, it is also possible to present them as a pharmaceutical composition. Accordingly, provided herein are pharmaceutical compositions which comprise one or more oligosaccharides disclosed herein, or one or more pharmaceutically acceptable salts, prodrugs, or solvates thereof, together with one or more pharmaceutically acceptable carriers thereof and optionally one or more other therapeutic ingredients.

The disclosure contemplates non-naturally occurring formulations of 3'SL and/or 6'SL. For example, the formulation can lack one or more components found in human milk such as, but not limited to proteins (e.g., antibodies, lactoferrin, mucins, growth factors), lipids (e.g., DHA, AA, FAA) and/or lactose. In some embodiments, the compositions of the disclosure comprises, consists essentially of or consists of 3'SL and/or 6'SL, wherein the 3'SL and/or 6'SL is at least 50%, 60%, 70%, 80%, 90%, 95%, 98%, 99% or 100% free of any other human milk component. In some embodiments, the composition comprising, consisting essentially of or consisting of 3'SL and/or 6'SL is in the form of a nutraceutical or pharmaceutical. In some embodiment, a composition comprising, consisting essentially of or consisting of 3'SL and/or 6'SL is in a freeze dried preparation such that it can be added to a liquid or beverage.

In certain embodiment, the oligosaccharide (e.g., 3'SL and/or 6'SL) in powder, liquid or bar form may be included into a nutritional formula. The compositions may comprise any amount of 3'SL and/or 6'SL effective for treating and/or preventing atherosclerosis and/or hyperlipidemia when enterally administered to an individual.

In a nutritional formula, the nutritional formula may comprise: 1) 3'SL and/or its derivatives, isomers, analogs and/or variants, and/or 6'SL and/or its derivatives, isomers, analogs and/or variants.

The 3'SL and/or 6'SL may be in powder or liquid form and/or may be included into a nutritional formula (e.g., a food or drink fortified with 3'SL and/or 6'SL). The compositions may comprise any amount of 3'SL and/or 6'SL and/or their derivatives, isomers, analogs and/or variants effective for treating and/or preventing atherosclerosis and/or hyperlipidemia when enterally administered to an individual.

Proper formulation is dependent upon the route of administration chosen. Any of the well-known techniques, carriers, and excipients may be used as suitable and as understood in the art; e.g., in Remington's Pharmaceutical Sciences. The pharmaceutical or nutraceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Delivery Technology, Rathbone et al., Eds., Drugs and the Pharmaceutical Science, Marcel Dekker, Inc.: New York, N.Y., 2002; Vol. 126).

The compositions of disclosure include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The compositions may conveniently be presented in unit dosage form and may be prepared by any of the methods well known in the art of pharmacy. Typically, these methods include the step of bringing into association one or more oligosaccharides of the disclosure or pharmaceutically salts, prodrugs, or solvates thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

The compositions include those suitable for oral administration. The compositions may conveniently be presented in unit dosage form and may be prepared by any of the methods well known in the art of pharmacy. Typically, these methods include the step of bringing into association a compound of the subject invention or a pharmaceutically salt, prodrug, or solvate thereof ("active ingredient") with the carrier which constitutes one or more accessory ingredients. In general, the compositions are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; as an oil-in-water liquid emulsion or a water-in-oil liquid emulsion; or as a chewable formulation (e.g., a gelatin based gummy). The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

In certain embodiments, diluents are selected from the group consisting of mannitol powder, spray dried mannitol, microcrystalline cellulose, lactose, dicalcium phosphate, tricalcium phosphate, starch, pregelatinized starch, compressible sugars, silicified microcrystalline cellulose, and calcium carbonate.

In certain embodiments, surfactants are selected from the group consisting of Tween 80, sodium lauryl sulfate, and docusate sodium.

In certain embodiments, binders are selected from the group consisting of povidone (PVP) K29/32, hydroxypropylcellulose (HPC), hydroxypropylmethylcellulose (HPMC), ethylcellulose (EC), corn starch, pregelatinized starch, gelatin, and sugar.

In certain embodiments, lubricants are selected from the group consisting of magnesium stearate, stearic acid, sodium stearyl fumarate, calcium stearate, hydrogenated vegetable oil, mineral oil, polyethylene glycol, polyethylene glycol 4000-6000, talc, and glyceryl behenate.

In certain embodiments, sustained release polymers are selected from the group consisting of POLYOX® (poly (ethylene oxide), POLYOX® N6OK grade, Kollidon® SR, HPMC, HPMC (high viscosity), HPC, HPC (high viscosity), and Carbopol®.

In certain embodiments, extended/controlled release coating are selected from a group of ethylcellulose polymers, such as ETHOCEL™ and Surelease® Aqueous Ethylcellulose Dispersions.

In certain embodiments, antioxidants are selected from a group consisting of butylated hydroxyanisole (BHA), butylated hydroxytoluene (BHT), sodium ascorbate, and α-tocopherol.

In certain embodiments, tablet coatings are selected from the group of Opadry® 200, Opadry® II, Opadry® fx, Opadry® amb, Opaglos® 2, Opadry® tm, Opadry®, Opadry® NS, Opalux®, Opatint®, Opaspray®, Nutraficient®.

Oligosaccharides may be administered orally at a dose of from 5 to 5000 mg/kg per day. The dose range for adult humans is generally from 50 mg to 2 g/day. Tablets or other forms of presentation provided in discrete units may conveniently contain an amount of one or more compounds which is effective at such dosage or as a multiple of the same, for instance, units containing 500 mg to 500 mg.

The oligosaccharides of the disclosure may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use; or alternatively may be mixed with a beverage (e.g., milk, juice, etc.) such that a nutraceutical formulation is prepared. Extemporaneous injection solutions and suspensions may be prepared from sterile powders, granules and tablets of the kind previously described.

Formulations for parenteral administration include aqueous and non-aqueous (oily) sterile injection solutions of the oligosaccharides which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the oligosaccharides to allow for the preparation of highly concentrated solutions.

In addition to the formulations described previously, the oligosaccharides may also be formulated as a depot preparation. Such long acting formulations may be administered by implantation (for example subcutaneously or intramuscularly) or by intramuscular injection. Thus, for example, the oligosaccharides may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose.

For administration by inhalation, oligosaccharides may be delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the oligosaccharides according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

Oligosaccharides may be administered orally or via injection at a dose of from 5 to 5000 mg/kg per day. The dose range for adult humans is generally from 50 mg to 2 g/day. Tablets or other forms of presentation provided in discrete units may conveniently contain an amount of one or more oligosaccharides which is effective at such dosage or as a multiple of the same, for instance, units containing 50 mg to 500 mg.

The amount of active ingredient that may be combined with the carrier materials to produce a single dosage form will vary depending upon the host treated and the particular mode of administration.

The oligosaccharides can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the disorder being treated. Also, the route of administration may vary depending on the disorder and its severity.

In the case wherein the patient's condition does not improve, upon the doctor's discretion the administration of the Oligosaccharides may be administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of the oligosaccharides may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disorder is retained. Patients can, however, require intermittent treatment on a long-term basis upon any recurrence of symptoms.

Disclosed herein are methods for treating or attenuating atherosclerosis and/or hyperlipidemia comprising administering to the subject having or suspected of having atherosclerosis and/or hyperlipidemia, a therapeutically effective amount of a composition comprising one or more oligosaccharides of the disclosure or pharmaceutically acceptable salts, solvates, or prodrugs thereof. Complications of atherosclerosis and hyperlipidemia, include, but are not limited to, and complications resulting therefrom, including, but not limited to, coronary artery disease, heart failure, myocardial infarction, aneurysm, stroke, arrhythmia, peripheral arterial disease, chronic kidney disease, end-stage renal disease, renal artery stenosis, central retinal artery occlusion, central retinal vein occlusion, branch retinal artery occlusion, branch retinal vein occlusion, erectile dysfunction, and mesenteric ischemia.

In certain embodiments, a method of treating or attenuating atherosclerosis and/or lipidemic comprises administering to the subject a therapeutically effective amount of one or more oligosaccharides as disclosed herein, or pharmaceutically acceptable salts, solvates, or prodrug thereof, so as to affect: (1) a decrease in the incidence or severity of the atherosclerosis; (2) a decrease in the size of aortic plaques; (3) a decrease in the size of atherosclerotic lesions; (4) a decrease in the plasma concentration for triglycerides; (5) a decrease in the plasma concentration of cholesterol; (6) reduced incidence of complications resulting from atherosclerosis and/or hyperlipidemia; and/or (7) an improvement in patient-reported outcomes as to the status of the patient's health condition.

Besides being useful for human treatment, certain oligosaccharides and formulations disclosed herein may also be useful for veterinary treatment of companion animals, exotic animals and farm animals, including mammals, rodents, and the like. More preferred animals include horses, dogs, and cats.

The compositions disclosed herein may also be combined or used in combination with other drugs and agents useful in the treatment of atherosclerosis and/or hyperlipidemia and complications resulting therefrom. Or, by way of example only, the therapeutic effectiveness of one of the oligosaccharides described herein may be enhanced by administration of an adjuvant (i.e., by itself the adjuvant may only have minimal therapeutic benefit, but in combination with another therapeutic agent, the overall therapeutic benefit to the patient is enhanced).

Such other agents, adjuvants, or drugs, may be administered, by a route and in an amount commonly used therefor, simultaneously or sequentially with a compound as disclosed herein. When a compound as disclosed herein is used contemporaneously with one or more other drugs, a pharmaceutical composition containing such other drugs in addition to the compound disclosed herein may be utilized, but is not required.

Thus, in another aspect, certain embodiments provide methods for treating or attenuating atherosclerosis and/or hyperlipidemia, and complications resulting therefrom, in a human or animal subject in need of such treatment comprising administering to said subject an amount of one or more oligosaccharides of the disclosure that is effective to reduce or prevent said disease or disorder in the subject, in combination with at least one additional agent for the treatment of said disorder that is known in the art. In a related aspect, certain embodiments provide therapeutic compositions comprising at least one oligosaccharide disclosed herein in combination with one or more additional agents for the treatment or attenuation of atherosclerosis and/or hyperlipidemia and complications resulting therefrom.

In certain embodiments, the oligosaccharides disclosed herein can be combined with one or more drugs or therapeutic agents that include, but is not limited to, cholesterol medications, anti-platelet medications, beta blocker medications, angiotensin-converting enzyme (ACE) inhibitors, calcium channel blockers, and diuretics.

In other embodiments, the oligosaccharides disclosed herein can be combined with one or more cholesterol medications selected from: HMG CoA reductase inhibitors, including, but not limited to, atorvastatin, fluvastatin, lovastatin, pravastatin, rosuvastatin calcium, and simvastatin; selective cholesterol absorption inhibitors, including but not limited to, ezetimibe; bile acid sequestrants, including but not limited to, cholestyramine, colestipol, and colesevelam HCl; fibrates, including but not limited to, gemfibrozil, fenofibrate, and clofibrate; niacin; and omega-3 fatty acid ethyl esters.

In yet other embodiments, the oligosaccharides disclosed herein can be combined with one or more anti-platelet medications selected from: acetylsalicylic acid, clopidogrel, prasugrel, and ticagrelor.

In certain embodiments, the oligosaccharides disclosed herein can be combined with one or more beta blocker medications selected from: acebutolol, atenolol, betaxolol, bisoprolol fumarate, carteolol, esmolol, labetalol, metoprolol, nadolol, nebivolol, penbutolol, pindolol, propranolol, sotalol, and timolol.

In other embodiments, the oligosaccharides disclosed herein can be combined with one or more ACE inhibitors selected from: benazepril, captopril, enalapril, fosinopril, lisinopril, moexipril, perindopril, quinapril, ramipril, and trandolapril.

In yet other embodiments, the oligosaccharides disclosed herein can be combined with one or more calcium channel blockers selected from: amlodipine, diltiazem, isradipine, nicardipine, nifedipine, nisoldipine, and verapamil.

In certain embodiments, the oligosaccharides disclosed herein can be combined with one or more diuretics selected from: chlorothiazide, chlorthalidone, indapamide, hydrochlorothiazide, methylclothiazide, metolazone, bumetanide, furosemide, ethacrynate, torsemide, amiloride hydrochloride, spironolactone, and triamterene.

The oligosaccharides disclosed herein can also be administered in combination with other classes of compounds, including, but not limited to, norepinephrine reuptake inhibitors (NRIs) such as atomoxetine; dopamine reuptake inhibitors (DARIs), such as methylphenidate; serotonin-norepinephrine reuptake inhibitors (SNRIs), such as milnacipran; sedatives, such as diazepham; norepinephrine-dopamine reuptake inhibitor (NDRIs), such as bupropion; serotonin-norepinephrine-dopamine-reuptake-inhibitors (SNDRIs), such as venlafaxine; monoamine oxidase inhibitors, such as selegiline; hypothalamic phospholipids; endothelin converting enzyme (ECE) inhibitors, such as phosphoramidon; opioids, such as tramadol; thromboxane receptor antagonists, such as ifetroban; potassium channel openers; thrombin inhibitors, such as hirudin; hypothalamic phospholipids; growth factor inhibitors, such as modulators of PDGF activity; platelet activating factor (PAF) antagonists; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; MTP Inhibitors; potassium channel activators; alpha-muscarinic agents; beta-muscarinic agents, such as carvedilol and metoprolol; antiarrhythmic agents; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as paclitaxel, docetaxel, and epothilones A-F; plant-derived products, such as *vinca* alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more oligosaccharides disclosed herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

EXAMPLES

Isolation of Pooled Human Milk Oligosaccharides From Human Breast Milk.

Oligosaccharides are extracted, reduced and purified according to the procedure described in Ninonuevo et al., (*Journal of Agricultural and Food Chemistry* 54(20):7471-7480 (2006)). Briefly, each milk sample (0.5 mL) is centrifuged at 3500 rpm at 4° C. for 30 mins and extracted with 10 mL (2:1) of a chloroform-methanol solution (v/v) and 2 mL deionized water. The emulsion is centrifuged at 3500 rpm at 4° C. for 30 mins and the lower chloroform layer is discarded. The upper layer is collected; the proteins are precipitated with 7 mL cold ethanol at 4° C. for 16 hours. The solution is centrifuged at 4° C. for 30 mins, the supernatant is recovered, dried and used for oligosaccharide analysis. Each oligosaccharide rich fraction is re-dissolved in 500 µL of deionized water and reduced using 500 µL of 2.0 M sodium borohydride in deionized water and incubated at 42° C. for 16 hours. The oligosaccharide solution is desalted and purified using the above-mentioned procedure.

HMO Fractionation by Two-Dimensional Chromatography.

Pooled HMO are separated by charge using anion exchange chromatography over QAE gravity columns (Sigma Aldrich, St. Louis, Mo., USA). Lyophilized pooled HMO were dissolved in 2 mM Tris and applied to equilibrated columns. Neutral, −1, −2, −3 and −4 charged HMO were eluted with 2 mM Tris containing 0, 20, 70, 100 and 400 mM NaCl, respectively. Tris and NaCl were removed by gel filtration chromatography over a P2 column. Separation is monitored by fluorescence high-performance liquid chromatography (HPLC-FL) as described below. Differently charged HMO fractions are further separated by size using P2 gel filtration chromatography (100 cm×16 mm) and monitored by HPLC-FL. Fractions that contained the same, but no other HMO are pooled and lyophilized.

Oligosaccharide Profiling by HPLC.

The dried oligosaccharide rich fraction from above is re-constituted with 50 µL deionized water and diluted 500 times with 50% acetonitrile:water in 0.1% formic acid prior to HPLC-Chip TOF MS analysis. Oligosaccharides are analyzed using an Agilent 1200 Series HPLC-Chip system (Santa Clara, Calif.) equipped with a chip consisting of 40 nL enrichment column and 43×0.75 mm ID analytical column, both packed with porous graphitized carbon 5 µm stationary phase. A nanoliter pump gradient is delivered at 0.3 µL/min consisting of (A) 3.0% acetonitrile:water in 0.1% formic acid and (B) 90% acetonitrile:water in 0.1% formic acid. A 45-minute LC gradient is run from 0-16% B, 2.5-20.0 mins, 16-44% B, 20.0-30.0 mins, 44-100% B, 30.0-35.0 mins with equilibration time of 20 mins at 0% B. Data is acquired in the positive ionization mode with a mass range of m/z 500-3000. Data analysis is performed using Analyst QS 1.1 software and the deconvoluted lists of masses are generated using Mass Hunter (Molecular Feature Extraction) software. Oligosaccharides are identified using a Glycan Finder program (in-house) written in Igor Pro version 5.04B software (WaveMetrics, Portland, Oreg.).

Studies Looking at 3'SL Effects on Bone Marrow-Derived Macrophages (BMDM).

Initial results indicated that 3'SL both in the absence and presence of LPS engaged with plasma membrane proteins on BMDM to regulate down-stream activation of the MAPK pathway but not the NFK-β pathway. This evidence suggests that 3'SL does not compete with LPS for its binding to Toll-like receptor 4 (TLR4). To elucidate the receptor, signaling pathway and downstream transcription regulated by 3'SL in BMDM, a three-prong approach is utilized: (a) Whole Transcriptome Shotgun Sequencing (WTSS) is used to identify differentially regulated genes. The set of differentially expressed genes are analyzed by gene-ontology and pathway analysis as well promoter analysis of up- and down-regulated genes (HOMER software) to identify the dominant receptor pathway activated and/or inhibited by 3'SL; (b) Phospho-kinase arrays are used to identify downstream signaling pathways. In both approaches, naive BMDM is compared with 3'SL-treated BMDM as well LPS-stimulated BMDM and LPS-treated BMDM co-treated with 3'SL; and (c) A 3'SL affinity matrix is generated to run macrophage plasma membrane and isolate 3'SL binding proteins. Proteins are eluted from the matrix using different salt gradients and analyzed by silvers staining. Relevant elution fraction and individual protein bands are isolated and prepared for mass-spectrometry analysis. The above three-way approach allows for the identification of the receptor, signaling pathway and downstream transcription that is regulated by 3'SL. To provide further confirmation for 3'SL mechanism of action with BMDM, CRISPR/Cas is used to knockout the identified receptor and signaling pathway identified from the three-prong approach detailed above.

A Short-Term Chronic Inflammation Model Using Rheumatoid Arthritis.

Preliminary results show that 3'SL attenuates LPS-induced M1 polarization and importantly its subsequent cytokine expression (IL-1b, IL-6, etc. mRNA and protein levels) in a mouse cell line, in primary mouse cells as well as in a human cell line. Here, the aim is to test whether the results translate to in vivo efficacy in a short-term and a long-term disease model of chronic inflammation. Rheumatoid arthritis (RA) is an inflammatory disorder that affects approximately 1% of the adult population worldwide. It is characterized by systemic and local inflammation that leads to cartilage and bone destruction. Collagen antibody-induced arthritis (CAIA) is a simple RA mouse model that can be used to address questions of pathogenic mechanisms and to screen candidate therapeutic agents. Arthritis is induced by the systemic administration of a cocktail of monoclonal antibodies that target various regions of collagen type II, which is one of the major constituents of articular cartilage matrix proteins, together with LPS. The high uptake rate in the CAIA model, and the capacity to synchronize the development of arthritis from the time of antibody injection, makes this model relatively straightforward.

RA Disease Model:

A cocktail of 4 monoclonal antibodies to type II collagen are injected IP on day 0 followed by an IP injection of LPS (50 mg) on day 3. Arthritis develops on day 4 and reaches its peak on days 7-8. Severity of arthritis in each limb is scored every third day in a blinded manner on a 0-4 scale. After 14 days animals will be sacrificed and hind-paw thickness are measured using electronic Vernier calipers. Hind limbs are processed for histology and sagittal sections across the heel are stained with H&E. The degree of inflammation in the synovial lining may be calculated by analyzing the mean density of several randomly selected areas in the medial aspect of the tibitarsal joint. The relative proportion of polymorphonuclear and mononuclear cells in each section at the bone-synovial junction are quantified and bone erosion are evaluated in a blinded manner using a modified 0-4 scoring criteria. For consistency, scoring is performed on the talus and tibia. Safranin O staining may be performed to demonstrate the destruction of surface cartilage, notably proteoglycan depletion (the red color indicates the presence of proteoglycan). The other hind limb is processed for both gene and protein expression analysis of macrophage markers and M1 and M2 macrophage markers.

3'SL Intervention:

Starting two days prior to antibody administration, mice receive 3'SL with the drinking water. Phenotypic outcome in the 3'SL intervention group are compared to animals that received drinking water alone, without 3'SL. Fifteen (15) mice will be used for each of the two groups (total of 30 mice).

In Vivo Atherosclerosis Mouse Model and 3'SL Intervention:

The complex pathology of atherosclerosis is characterized by the accumulation of lipids, inflammatory cells, and fibrous elements in large- and medium-sized arteries. According to the "response-to-retention" model, focal infiltration and retention of apolipoprotein B (apoB)-containing lipoproteins, such as low-density lipoproteins (LDLs), lipoprotein (a), and triglyceride-rich remnant particles (TRLs), in the subendothelial matrix of the tunica intima of arteries at atherosclerosis-prone sites initiates atherogenesis. Subsequent oxidation, lipolysis, proteolysis, and further aggregation of trapped LDL particles contribute to a chronic inflammatory response characterized by monocyte and T cell migration into the intima. Monocytes entering the plaque differentiate into macrophages and the expression of scavenger receptors result in internalization of modified lipoprotein particles. Lesion macrophages proliferate, accumulate massive amounts of cholesterol, and become lipid droplet-loaded "foam cells," resulting in their retention in the lesion. Atherosclerosis is further characterized by the accumulation of M1-like macrophages and secretion of characteristic cytokines and chemokines. Priming of macrophages is sufficient to promote increased macrophage infiltration and inflammation in aorta, exacerbating atherosclerosis. Because of their low cholesterol levels, mice do not spontaneously develop atherosclerosis. Therefore, we will use $Ldlr^{-/-}$ mice with a hypercholesterolemic background to study atherosclerosis development, which has several advantages: (1) cholesterol in $Ldlr^{-/-}$ mice is mainly restricted to LDL particles resembling the situation in humans; (2) because of the minor importance of Ldlr in bone marrow derived cells related to atherosclerosis, the $Ldlr^{-/-}$ mice are a very suitable model to study the role of candidate genes in these cells; (3) initiation of atherosclerotic plaque development can be highly controlled, as atherosclerosis will develop only upon feeding a high-fat/high-cholesterol diet.

Male $Ldlr^{-/-}$ mice are maintained on regular chow. One group receives 3'SL with the drinking water, the control group receives drinking water alone, without 3'SL. Weight gain, and lipid and lipoprotein levels (LDL, VLDL and HDL) as well as plasma 3'SL levels will be measured using established methods, such as the method described in Foley et al. (*Arterioscler Thromb Vasc Biol.* 33:2065-74 (2013)). Groups of 10 mice for each of the two groups are sacrificed after 6 and 16 weeks of 3'SL treatment to compare early and advanced atherosclerosis development (total of 40 mice).

Atherogenesis is determined by "en face" preparation of the entire aorta and Sudan IV staining to determine lipid infiltration as a measure for lesion surface as described in Gordts et al. (*Arterioscler Thromb Vasc Biol.* 29:1258-64 (2009)). In addition, the heart is isolated for sectioning of the aortic root to determine aortic root lesion area and qualitative assessment of the plaque phenotype. Aortic root cross-sectional atherosclerosis is measured by cutting 10 μm paraffin sections starting at the aortic valve plane and covering 1,000 μm in 100-μm increments. Two approaches are used to assess if 3'SL administration affects plaque stability and inflammatory cell composition in atherosclerotic plaques. Sections are immunostained using various antibodies to identify smooth muscle cells and macrophages and apoB content as well as the presence of oxidation-specific antibodies reflective of OxLDL. The extracellular content is visualized via staining using Oil red O (lipids), Hematoxylin and Eosin (necrotic core), Movat Pentachrome (proteoglycans), Masson-Goldner (collagen) and Verhoeffs van Gieson (elastin) staining protocols. As a measurement of the clinically relevant plaque vulnerability/stability in advanced lesions, fibrous cap thickness is determined by comparing serial sections each stained for smooth muscle cells and collagens, and the extent of necrosis will be quantified using imaging techniques as described in Gordts P L et al. (*Cell Metabolism* 20:813-26 (2014)). In a second approach, flow cytometry is used to analyze immune cells in the lesions according to Kolstova et al. (*Circ Res* 111:1274-85 (2012)). The first approach gives a crude assessment of inflammatory cell composition in atherosclerotic lesions. The second approach allows a much better quantification and better resolution in determining subsets of lymphocytes.

A number of embodiments have been described herein. Nevertheless, it will be understood that various modifications may be made without departing from the spirit and scope of this disclosure. Accordingly, other embodiments are within the scope of the following claims.

What is claimed is:

1. A method of decreasing the size of aortic plaques or atherosclerotic lesions in a subject, in need thereof, the method comprising administering a composition comprising 3' sialyllactose and 6' sialyllactose at an amount effective to significantly reduce atherosclerotic lesions or aortic plaque size by suppressing inflammation caused by macrophages.

2. The method of claim 1, further comprising administering the composition in combination with one or more drugs or therapeutic agents selected from cholesterol medications, anti-platelet medications, beta blocker medications, angiotensin-converting enzyme (ACE) inhibitors, calcium channel blockers, and diuretics.

3. The method of claim 1, wherein the subject has one or more complications associated with atherosclerosis the one or more complications associated with atherosclerosis and/or hyperlipidemia are selected from coronary artery disease, heart failure, myocardial infarction, aneurysm, stroke, arrhythmia, peripheral arterial disease, chronic kidney disease, end-stage renal disease, renal artery stenosis, central retinal artery occlusion, central retinal vein occlusion, branch retinal artery occlusion, branch retinal vein occlusion, erectile dysfunction, and mesenteric ischemia.

4. The method of claim 1, wherein the 3'-sialyllactose and 6'sialyllactose and pharmaceutically acceptable salts.

5. The method of claim 4, wherein the pharmaceutically acceptable salts are sodium salts.

* * * * *